| United States Patent [19] | [11] | 4,242,451 |
|---|---|---|
| Ehrenthal Irving et al. | [45] | Dec. 30, 1980 |

[54] METHOD OF TREATMENT OF FLOCCULATED HOMOGENATE OF MICROBIAL CELLS CONTAINING GLUCOSE ISOMERASE

[75] Inventor: Irving Ehrenthal, University City; Kenneth K. Shieh, St. Louis County; Barrett L. Scallet, Clayton; Jagdish Rajpara, St. Louis, all of Mo.

[73] Assignee: Anheuser-Busch, Incorporated, St. Louis, Mo.

[21] Appl. No.: 88,013

[22] Filed: Oct. 25, 1979

Related U.S. Application Data

[63] Continuation-in-part of Ser. No. 859,294, Dec. 12, 1977, abandoned.

[51] Int. Cl.³ ........................ C12P 19/24; C12N 11/14
[52] U.S. Cl. ................................... 435/94; 435/176; 435/827
[58] Field of Search .................................. 435/94, 176

[56] References Cited

U.S. PATENT DOCUMENTS

| 3,838,007 | 9/1974 | Van Velzen | 195/68 |
|---|---|---|---|
| 3,935,069 | 1/1976 | Long | 195/31 F |
| 3,980,521 | 9/1976 | Amotz et al. | 195/68 |
| 3,989,597 | 11/1976 | Lee et al. | 195/56 |
| 4,001,082 | 1/1977 | Tsumura et al. | 195/31 F |
| 4,060,456 | 11/1977 | Long | 195/31 F |
| 4,138,290 | 2/1979 | McMullen | 435/94 |
| 4,144,127 | 3/1979 | Enokizono et al. | 435/176 |

*Primary Examiner*—Lionel M. Shapiro
*Attorney, Agent, or Firm*—Gravely, Lieder & Woodruff

[57] ABSTRACT

This application concerns a method for treating a flocculated homogenate of whole cell glucose isomerase derived from the microorganism Actinoplanes so that the preparation can be dried, preferably after being extruded into cylindrically-shaped particles. The critical step in this method is the addition of a water absorbing smectite filler to the flocculated homogenate prior to drying. The floc also may be frozen and thawed prior to addition of the filler.

21 Claims, No Drawings

METHOD OF TREATMENT OF FLOCCULATED HOMOGENATE OF MICROBIAL CELLS CONTAINING GLUCOSE ISOMERASE

REFERENCE TO PRIOR APPLICATIONS

This application is a continuation-in-part of prior copending application Ser. No. 859,294 filed Dec. 12, 1977, now abandoned.

BACKGROUND OF THE INVENTION

Amotz et al, U.S. Pat. No. 3,980,521, discloses a method of preparing a water insoluble glucose insomerase product by concentrating and homogenizing microorganism cells to form a homogenized cell concentrate containing ruptured cells, reacting the homogenized concentrate with glutaraldehyde to form a coherent solid product and removing water and shaping the coherent product into a divided form.

Lee et al, U.S. Pat. No. 3,821,086 discloses a process for converting glucose to fructose by contacting a glucose substrate with flocculated whole microbial cells containing glucose isomerase. The whole microbial cells are previously flocculated by means of a polyelectrolyte flocculating agent.

Long, U.S. Pat. No. 3,989,596 discloses a method of forming an enzyme-containing aggregate comprising the steps of flocculating microbial cells and their associated enzymes with a synthetic polyelectrolyte flocculating agent, and drying the aggregate.

Lee, U.S. Pat. No. 3,989,597 discloses a method of forming an enzyme containing aggregate comprising the steps of flocculating microbial cells and their associated enzymes with a synthetic polyelectrolyte flocculating agent, freezing the aggregate, then thawing and crushing the aggregate.

Lee, U.S. Pat. No. 3,821,086, Long, U.S. Pat. No. 3,989,596, and Lee, U.S. Pat. No. 3,989,597 also state that the flocculated cells may be extruded into various shapes suitable for use in an enzymatic process.

The processes disclosed in these patents are unsuitable for preparing immobilized glucose isomerase derived from the microorganism Actinoplanes, specifically *Actinoplanes missouriensis*. Homogenized *Actinoplanes missouriensis* cells are difficult to dry and particularly are difficult to extrude because of their excessive retentivity of water. The retained water cannot be removed effectively by conventional drying means.

Accordingly, it is a principal object of the present invention to provide a process whereby flocculated homogenized *Actinoplanes missouriensis* cells can be dewatered to provide a dried immobilized enzyme.

SUMMARY OF THE INVENTION

This invention involves a process for treating a flocculated homogenate of whole cell glucose isomerase derived from the microorganism Actinoplanes in order to dry the homogenate so that the enzyme is immobilized and usable in converting glucose to fructose. The critical step in this process is the addition of a water absorbing smectite filler to the flocculated homogenate prior to drying and/or extrusion. In order to improve the extrusion characteristics of the flocculated homogenate, the floc may be frozen and thawed prior to addition of the filler.

DETAILED DESCRIPTION

Whole microbial cells containing glucose isomerase are prepared from a microorganism of the genus Actinoplanes, more specifically *Actinoplanes missouriensis*. Methods for growing these cells are disclosed in U.S. Pat. Nos. 3,834,988, 3,992,262, and 4,003,793.

A whole cell slurry is then homogenized in such a way that a substantial proportion of the cells is disrupted. The slurry is preferably passed through a Manton-Gaulin homogenizer 2 or 3 times at a pressure of 2000–9000 psi. Means other than homogenization may be used to disrupt the cells.

A cobalt salt may be added before or after the cell disruption treatment. The concentration of cobalt ions should not exceed 100 ppm. However, addition of cobalt salt is not essential to successfully practice the process of this invention.

A flocculant is then added to the homogenate. Flocculants suitable for this invention are cationic polyelectrolytes. Preferred flocculants are Cat-floc from Calgon Co. and Magnifloc 581C from American Cyanamid Co. The concentration of flocculant should range from 20% to 90%, based on the dry weight of the cells.

The flocculated homogenate is collected by filtration. The floc may then be frozen at about $-10°$ to $-15°$ C. If this treatment is used, the floc is maintained at this temperature for about three to about five hours to make sure that complete freezing takes place. Any other treatment which assures complete freezing is satisfactory.

It appears that the freezing step, if used, changes the physical structure of the filtered floc so that additional water is released. This release of water increases the solids concentration of the floc.

The frozen floc is then thawed, after which additional water is expressed from the flocculated enzyme, whole cell, and cell debris mixture. The floc is dewatered to a level of about 30% to about 35% solids. It should be noted that the freezing-thawing procedure is not necessary to achieve the results of this invention. However, this procedure does improve the extrusion characteristics of the flocculated homogenate when relatively high proportions of cells have been disrupted. At lower levels of cell disruption, satisfactory dewatering (after flocculation) is obtained without the freeze-thaw treatment.

Whether or not the freezing-thawing procedure is employed, a water absorbing filler is then added to the floc. The addition of filler allows effective extrusion. Suitable fillers include bentonite, montmorillonite, and other clays of the smectite group. Addition of carbon to the filler shows some increase in the porosity of the extruded particle.

The filler acts to absorb water from the floc, thus allowing it to be dried more readily. Furthermore, addition of the filler improves the consistency of the floc, thus allowing it to be more easily extruded. The preferred level of filler ranges from 10% to 25%, based on the weight of the floc.

In a preferred embodiment of the invention the dewatered filler-treated enzyme-containing floc can be extruded without difficulty through dies having cylindrical openings of about 1 to about 2 mm. diameter. The extruded particles are dried, preferably in an air oven at 55°–60° C. for one to two hours.

The dried extruded particles are cut to a length of 5–8 mm. The cylindrical particles are then milled and sieved to a granular shape. These granules have a length on the order of about 0.8–1.2 mm.

For use, the granular particles are packed into a jacketed column, which is maintained at about 60° to 65° C. A dextrose solution of about 43 to 50% (d.s.), and about pH 7.5, containing about 7 mM $Mg^{++}$ and about 250 ppm $SO_2$ is pumped continuously through the column, and the product analyzed for fructose. From this analysis the half-life of the particles can be determined. The half-life at 65° C. ranges from about 30 to about 35 days; at 60° C., the half-life may be as long as about 60 days or more.

The floc to which the smectite has been added also can be dried by being placed in a fluidized bed dryer and the dried immobilized enzyme particles then are ground to the desired size, that is, about 16 to 20 mesh. The smectite treated floc also can be tray dried and ground to the proper particle size, but this is not as advantageous as fluidized bed drying, because the fluidized bed dryer acts to break the homogenate into smaller pieces, thus reducing the final grinding requirements.

EXAMPLE 1

A washed whole-cell slurry of *Actinoplanes missouriensis* containing glucose isomerase, and comprising about 5% cells on a dry solids basis, was homogenized by passing it through a Manton-Gaulin homogenizer. The slurry (1.7 liters) was put through the homogenizer three times at 8000–9000 psi.

EXAMPLE 2

A washed whole-cell slurry of *Actinoplanes missouriensis* containing glucose isomerase and comprising about 5% cells on a dry solids basis, was homogenized by passing it through a Manton-Gaulin homogenizer. The slurry (7 liters) was put through the homogenizer two times at 8000–9000 psi.

To the thus-treated homogenate was added 10 liters of a 2.2% solution of Cat-floc. The flocculated homogenate was then filtered and mixed with 12.5% bentonite (based on solids content of cake) to improve extruding characteristics of the floc.

EXAMPLES 3–6

Different concentrations of bentonite were added to portions of the dewatered floc of Example 1 prior to extrusion. The flocculated homogenate, after being treated with bentonite, was extruded through die openings of various sizes. After the extrusion step, the extruded particles were dried and cut to 5–8 mm lengths.

The following table demonstrates the activities of the extruded flocculated homogenate at various concentrations of bentonite.

TABLE I

| Example | Filler (% bentonite) | Extruder Die Size (mm) | Solids % | IGIU/gram (d.s.b) |
|---|---|---|---|---|
| 3 | 12.0 | 2.0 | 90.7 | 330 |
| 4 | 16.7 | 2.0 | 90.9 | 280 |
| 5 | 25.0 | 2.0 | 90.7 | 280 |
| 6 | 15 | 1.5 | 94.00 | 350 |

The activity values were determined by passing a dextrose substrate containing 43–45% solids through a column packed with the extruded particles. The reaction conditions may be summarized as follows:

| (1) | pH of substrate | 7.5 |
|---|---|---|
| (2) | additives to substrate | $Mg^{++}$ 7mM $SO_2$ 250 ppm |
| (3) | temperature | 64°–65° C. |
| (4) | reactor | jacketed; 1.6 × 20cm |
| (5) | flow direction | downward |

EXAMPLES 7–15

Portions of flocculated homogenate as prepared in Example 1 were mixed with a suitable filler (bentonite or montmorillonite), extruded through die openings of various diameters, dried, and cut to dimension of 5–8 mm length. These particles were then milled and sieved, and the effects on enzyme activity of the milling step were measured. The results of this additional step are shown in Table II.

TABLE II

| Example | % Filler | Preparation | Extruder Die Size (mm) | Particle Length (mm) | IGIU/g (d.s.b.) |
|---|---|---|---|---|---|
| 7 | 12% Bentonite | Extruded; not milled | 2.0 | 5–8 | 327 |
| 8 | 12% Bentonite | Extruded; milled | 2.0 | 0.8–1.2 | 766 |
| 9 | 12% Bentonite | Extruded; milled | 2.0 | 0.6–0.8 | 1042 |
| 10 | 12% Bentonite | Extruded; milled | 2.0 | 0.3–0.4 | 1310 |
| 11 | 15% Bentonite | Extruded; not milled | 1.5 | 5–8 | 350 |
| 12 | 12.5% Bentonite | Extruded; not milled | 1.0 | 3–7 | 581 |
| 13 | 12.5% Bentonite | Extruded; milled | 1.0 | 0.8–1.2 | 750 |
| 14 | 10% Bentonite | Extruded; milled | 1.0 | 0.8–1.2 | 626 |
| 15 | 10% Montmorillonite | Extruded; milled | 1.0 | 0.8–1.2 | 617 |

From the foregoing Table, it can be seen that lightly milling the extruded particles increases enzyme activity.

EXAMPLES 16–20

Table III illustrates the pressure drop characteristics (extrapolated from laboratory column measurements) of various flocculated homogenized enzyme preparations. The enzyme preparations were made as in Example 1. The preparations were extruded through die openings of various sizes and were milled to lengths of 0.8–1.2 mm prior to use in the column.

TABLE III

| Example | Extruder Die Size (mm) | Filler | Pressure Drop (psi) 15 ft. column | 30 ft. column |
|---|---|---|---|---|
| 16 | 1.0 | 12% Bentonite | 1.5 | 6.0 |

TABLE III-continued

| Example | Extruder Die Size (mm) | Filler | Pressure Drop 15 ft. column | (psi) 30 ft. column |
|---|---|---|---|---|
| 17 | 1.5 | 15% Bentonite | 2.0 | 6.0 |
| 18 | 1.5 | 10% Bentonite 20% Carbon | 2.0 | 6.0 |
| 19 | 1.5 | 10% Bentonite 40% Carbon | 2.0 | 6.0 |
| 20 | 2.0 | 12% Bentonite | 2.0 | 12.0 |

From the foregoing table, it is apparent that the extruded filler-treated preparations would exhibit good flow properties in industrial scale column reactors.

EXAMPLES 21-24

Table IV shows the activities of extruded enzyme containing particles prepared with various diluents, specifically, filter-aid (Celite 560 from Johns-Manville) and carbon (Darco G-60 from ICI-USA). The diluents are added to the flocculated homogenate along with the water-absorbing filler.

TABLE IV

| Example | % Filler | Preparation | Extruder Die Size (mm) | Particle Length (mm) | IGIU/g (d.s.b.) |
|---|---|---|---|---|---|
| 21 | 10% Bentonite 40% Celite 560 | Extruded; milled | 1.0 | 0.8-1.2 | 653 |
| 22 | 10% Bentonite 20% Carbon (Darco G-60) | Extruded; milled | 1.0 | 0.8-1.2 | 800 |
| 23 | 10% Bentonite 40% Carbon (Darco G-60) | Extruded; milled | 2.0 | 0.8-1.2 | 729 |
| 24 | 10% Bentonite 40% Carbon (Darco G-60) | Extruded only | 1.0 | 5-8 mm | 553 |

An increase in available activity can be observed when carbon is added as a diluent to the bentonite treated enzyme preparation (Examples 21-23). Examples 23 and 24 show the effect of milling and diameter on activity.

EXAMPLES 25-26

Flocculated homogenate was prepared and mixed with a filler as shown in Example 2. The mass was then extruded through either 1 mm or 2 mm die openings. The extruded cylinders were dried, cut to lengths of 5-8 mm, put through a small laboratory mill and screened so that final length was about 0.8 to about 1.2 mm. Table V gives the activities of these preparations.

TABLE V

| Example | % Filler | Preparation | Extruder Die Size (mm) | Particle Length (mm) | IGIU/g (d.s.b.) |
|---|---|---|---|---|---|
| 25 | 12.5% Bentonite | Extruded; | 1.0 | 0.8-1.2 | 739 |
| 26 | 12.5% Bentonite | Extruded; milled | 2.0 | 0.8-1.2 | 828 |

EXAMPLE 27

A washed whole-cell slurry of *Actinoplanes missouriensis* containing glucose isomerase and comprising about 5% cells on a dry basis, was homogenized by passing it through a Crepaco homogenizer. The slurry (2 liters) was put through the homogenizer two times at 5000 psi.

To the thus treated homogenate was added 5.57 liters of a 2% solution of Cat-floc. The flocculated homogenate was then filtered, mixed with 12.5% bentonite (based on solids content of cake) and extruded. The extruded particles were dried in a fluidized bed dryer at 55° C. and milled to a particle size of 16-20 mesh. The material had an activity of 940 IGIU/g based on dry solids.

EXAMPLE 28

A washed whole cell slurry of *Actinoplanes missouriensis* containing glucose isomerase, and comprising about 5% cells on a dry solids basis, was homogenized using a Manton-Gaulin homogenizer at 8500-9000 psi. The whole cell isomerase slurry was passed through the unit 3 times.

Cationic flocculant (CAT-FLOC from Calgon Co.) was added to the homogenate. The agglomerate was collected by filtration over filter aid and frozen.

After thawing additional water was expressed from the flocculated enzyme and cell debris mixture so that the floc was effectively dewatered to 28-30% solids (d.s.b.). Then 12.5% bentonite (d.s.b.) was added and the mix was formed into disc shaped segments which were dried in a conventional tunnel dryer. The dried segments were ground to a particle size of 10-16 mesh.

When these particles were placed in a 1.6×20 cm downflow column and treated with a dextrose solution of 43-45% dry solids at pH 7.5 with 7 mM $Mg^{++}$ and 250 ppm $SO_2$ at 65° C., the material had an activity of 304 IGIU/g based on the dry solids.

EXAMPLE 29

The foregoing procedure of Example 28 was repeated except that the dried particles were ground to 16-20 mesh and the run tested 710 IGIU/gram.

EXAMPLE 30

A washed whole cell slurry of *Actinoplanes missouriensis* containing glucose isomerase, and comprising about 5% cells on a dry solids basis was homogenized using a Manton-Gaulin homogenizer at 8500-9000 psi. The whole cell isomerase slurry was passed through the unit 3 times.

Cationic flocculant (CAT-FLOC from Calgon Co.) was added to the homogenate. The agglomerate was collected by filtration over filter aid and frozen.

After thawing additional water was expressed from the flocculated enzyme and cell debris mixture so that the floc was effectively dewatered to 28-30% solids (d.s.b.). Then 12.5% bentonite (d.s.b.) was added and mixed. The mixture was dried in an air oven on trays. The dried particles were ground to a particle size of 16-20 mesh.

When these particles were placed in a 1.6×20 cm down-flow column and treated with a dextrose solution of 43-45% dry solids at pH 7.5 with 7 mM $Mg^{++}$ and 250 ppm $SO_2$ at 65° C., the material had an activity of 695 IGIU/g based on the dry solids.

EXAMPLE 31

A washed whole cell slurry of *Actinoplanes missouriensis* containing glucose isomerase, and comprising about 5% cells on a dry solids basis, was homogenized using a Manton-Gaulin homogenizer at 8500-9000 psi. The whole cell isomerase slurry was passed through the unit 2 times.

Cationic flocculant (CAT-FLOC from Calgon Co.) was added to the homogenate. The agglomerate was dewatered by centrifugation. Then 12.5% bentonite (d.s.b.) was added and the mix was placed in a fluidized bed dryer. The dried particles were milled to a particle size of 16-20 mesh.

When these particles were placed in a 1.6×20 cm down-flow column and treated with a dextrose solution of 43-45% dry solids at pH 7.5 with 7 mM $Mg^{++}$ and 250 ppm $SO_2$ at 65° C., the material had an activity of 694 IGIU/g based on the dry solids.

What is claimed:

1. A method of immobilizing glucose isomerase cell material obtained from whole microbial cells of an organism of the genus Actinoplanes containing glucose isomerase comprising the steps of
   a. disrupting a portion of whole microbial cells of the genus Actinoplanes containing glucose isomerase,
   b. flocculating said disrupted glucose isomerase cell material,
   c. adding a water absorbing smectite filler to said flocculated glucose isomerase cell material, and
   d. forming the mixture of glucose isomerase cell material and the water absorbing smectite filler into discrete particles.

2. The method of claim 1 wherein the microorganism is *Actinoplanes missouriensis*.

3. The method of claim 1 wherein the microbial cells are passed through a homogenizer two times at 2000 to 9000 psi.

4. The method of claim 1 wherein the disrupted glucose isomerase cell material is flocculated solely by means of a cationic flocculating agent.

5. The method of claim 1 wherein the filler is a montmorillonite.

6. The method of claim 1 wherein the filler is a bentonite.

7. The method of claim 1 wherein the smectite filler is added at a concentration of 10% to 25% by weight of the original whole microbial cells on a dry solids basis.

8. The method of claim 1 including the step of extruding the mixture of glucose isomerase cell material and smectite filler through a die, and milling the extruded particles to a length of less than about 1.2 mm.

9. The method of claim 1 including the step of drying the mixture of glucose isomerase cell wall material and smectite filler and grinding the dried particles to about 16 to about 20 mesh.

10. The method of claim 1 including the steps of freezing the flocculated disrupted glucose isomerase cell material, thawing said frozen cell material, and dewatering to less than about 35% solids prior to mixing with filler.

11. The method of claim 11 wherein the whole cells are homogenized by being passed through a homogenizer three times at 2000 to 9000 psi prior to flocculation.

12. An immobilized enzyme comprising a plurality of discrete particles each comprised of glucose isomerase cell material from an organism of the genus Actinoplanes in at least partially disrupted condition and a water absorbing smectite filler.

13. The product of claim 12 wherein the cells are derived from *Actinoplanes missouriensis*.

14. The product of claim 12 wherein the filler is a bentonite.

15. The product of claim 12 wherein the filler is a montomorillonite.

16. The product of claim 12 wherein the filler comprises 10% to 25% of the flocculated preparation on a dry solids basis and the particles are about 1 to about 2 mm in diameter and about 0.8 to about 1.2 mm in length.

17. The product of claim 12 wherein the particles are about 16 to about 20 mesh in size.

18. A process for converting glucose to fructose comprising contacting a glucose containing substrate with an immobilized glucose isomerizing enzyme of the genus Actinoplanes in solid particulate form comprising a mixture of a water absorbing smectite filler and glucose isomerase cell material of the genus Actinoplanes in at least partially disrupted condition.

19. The process of claim 18 wherein said cells are derived from *Actinoplanes missouriensis*.

20. The process of claim 18 wherein the filler is a montmorillonite.

21. The process of claim 18 wherein the filler is a bentonite.

* * * * *